United States Patent [19]

Röchricht et al.

[11] 4,329,341
[45] May 11, 1982

[54] 5-PHENYL-1,3,4,5-TETRAHYDRO-2H-1,4-BENZODIAZEPIN-2-ONES, AND PHARMACEUTICAL COMPOSITIONS CONTAINING THEM

[75] Inventors: Julianna Röchricht; Lajos Kisfaludy; Márton Kajtár; Éva Pálosi; László Szporny, all of Budapest, Hungary

[73] Assignee: Richter Gedeon Vegyeszeti Gyar Rt, Budapest, Hungary

[21] Appl. No.: 178,679

[22] Filed: Nov. 26, 1980

[51] Int. Cl.$^3$ .................... A61K 31/55; C07D 243/24
[52] U.S. Cl. .................. 424/244; 424/273 R; 424/274; 260/239.3 D
[58] Field of Search .............. 260/239.3 D; 424/244, 424/274, 273 R

[56] References Cited

U.S. PATENT DOCUMENTS 3,263,838  2/1966  Archer et al. ............... 260/239.3 D
4,045,433  8/1977  Röhricht et al. ............ 260/239.3 D

FOREIGN PATENT DOCUMENTS 48-25199  7/1973  Japan ..................... 260/239.3 D

*Primary Examiner*—Robert T. Bond
*Attorney, Agent, or Firm*—Keil & Witherspoon

[57] ABSTRACT

The invention relates to new optically active or racemic 5-phenyl-1,3,4,5-tetrahydro-2H-1,4-benzodiazepin-2-one derivatives of the general formula (I)

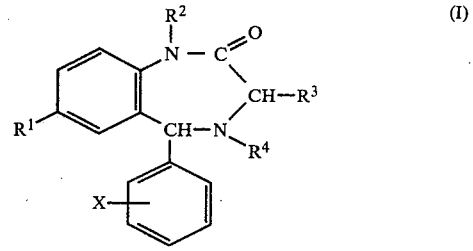

wherein
$R^1$ stands for hydrogen, halogen, trifluoromethyl or a nitro group;
$R^2$ stands for hydrogen or alkyl having 1 to 6 carbon atoms;
$R^3$ represents a group conventionally attached to the —CH(NH$_2$)—COOH group of the known optically active or racemic α-amino-acids, preferably an optionally substituted lower alkyl group;
$R^4$ is hydrogen, chlorocarbonyl or carbamoyl; and
X is hydrogen, halogen or trifluoromethyl, with the proviso that if in the racemic compounds $R^4$ stands for hydrogen $R^3$ is other than alkyl having 1 to 6 carbon atoms, in which the centers of asymmetry in the 3- and 5-positions have the same absolute configuration, and pharmaceutically acceptable acid addition salts thereof, and a process for their preparation. The new compounds show valuable enzyme inducing activity and can therefore be employed as active ingredients of pharmaceutical compositions, which are also within the scope of the present invention.

10 Claims, No Drawings

5-PHENYL-1,3,4,5-TETRAHYDRO-2H-1,4-BENZODIAZEPIN-2-ONES, AND PHARMACEUTICAL COMPOSITIONS CONTAINING THEM

This invention relates to new 5-phenyl-1,3,4,5-tetrahydro-2H-1,4-benzodiazepin-2-one derivatives and process for their preparation. More particularly, the invention concerns new optically active or racemic 5-phenyl-1,3,4,5-tetrahydro-2H-1,4-benzodiazepin-2-one derivatives, which contain centres of asymmetry in the 3- and 5-positions and in which said centres are in the same absolute configuration. The invention also includes a process for the preparation of said compounds and pharmaceutical compositions containing them.

The new 5-phenyl-1,3,4,5-tetrahydro-2H-1,4-benzodiazepin-2-one derivatives according to the invention are encompassed by the general formula (I)

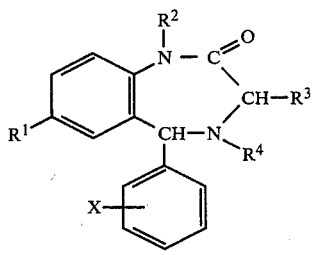

wherein
$R^1$ stands for hydrogen, halogen, trifluoromethyl or a nitro group;
$R^2$ is hydrogen or alkyl having 1 to 6 carbon atoms;
$R^3$ represents a group conventionally attached to the —CH(NH$_2$)—COOH group of the known optically active or racemic α-amino-acids, preferably an optionally substituted lower alkyl group;
$R^4$ is hydrogen, chlorocarbonyl or carbamoyl; and
X is hydrogen, halogen or trifluoromethyl,
with the proviso that if in a racemic compound of the general formula (I) $R^4$ represents hydrogen, $R^3$ does not stand for an unsubstituted lower alkyl group.

The pharmaceutically acceptable acid addition salts of the compounds of the general formula (I) are also within the scope of the present invention.

The term "halogen" used throughout the specification relates to fluorine, chlorine, bromine or iodine.

The term "alkyl having 1 to 6 carbon atoms" as used herein means straight or branched chained aliphatic hydrocarbon groups, having 1 to 6 carbon atoms (e.g. methyl, ethyl, n-propyl, isopropyl, n-butyl, sec.-butyl, tert.-butyl, n-pentyl, isopentyl, n-hexyl or isohexyl, etc.).

The term "a group conventionally attached to the —CH(NH$_2$)—COOH group of the known optically active or racemic α-amino-acids" preferably relates to methyl, isopropyl, benzyl-4-hydroxybenzyl, 3-indolylmethyl, etc. groups.

According to the invention compounds of the general formula (I) (in which $R^1$, $R^2$, $R^3$, $R^4$ and X have the same meaning as defined above) are prepared by reducing optically active or racemic dihydro-1,4-benzodiazepin-2-one derivatives of the general formula (II)

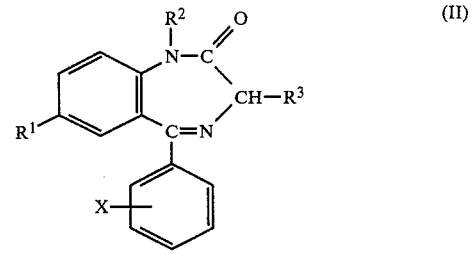

($R^1$, $R^2$, $R^3$ and X are as defined above), which contain a centre of asymmetry in the 3-position, and if desired, converting a compound of the general formula (I) obtained, in which $R^4$ represents a hydrogen atom ($R^1$, $R^2$, $R^3$ and X are as defined above) into an acid addition salt thereof and/or reacting it with an alkali metal cyanate or phosgene, and if desired, reacting a compound of the general formula (I) obtained by the reaction with phosgene, in which $R^4$ stands for chlorocarbonyl ($R^1$, $R^2$, $R^3$ and X are as defined above) with ammonia, and/or if desired, reacting a compound of the general formula (I) obtained, in which $R^2$ is hydrogen ($R^1$, $R^3$, $R^4$ and X are as defined above) and/or converting a compound of the general formula (I), in which $R^4$ is hydrogen ($R^1$, $R^2$, $R^3$ and X are as defined above) into a pharmaceutically acceptable acid addition salt thereof.

The compounds of the general formula (I) possess valuable enzyme inducing activity and are practically devoid of the sedative effect of the related compounds.

The most closely related tetrahydro-1,4-benzodiazepin-2-ones known in the art are unsubstituted in the 4-position and contain a lower alkyl group in the 3-position. Their preparation is for example disclosed in the following publications: the German Patent Specification No. 1,199,776 describes the catalytic hydrogenation of the corresponding dihydro-derivatives, and according to the U.S. Pat. No. 3,522,289 the compounds are prepared by intramolecular condensation of the aminoacetic acid esters N-substituted by an 2-aminobenzhydrile group. The Austrian Patent Specification No. 283,370 discloses a method along which the protecting group of the corresponding 2-amino-benzhydrole derivatives acylated by protected amino acids is splitted off by acydolysis, while according to the Austrian Patent Specification No. 311,356 the compounds are prepared from the corresponding aminobenzophenone derivatives acylated by protected amino acids by catalytic hydrogenation. Finally, the Austrian Patent Specification No. 309,439 discloses the resolution of racemic tetrahydro-1,4-benzodiazepin-2-ones containing a centre of asymmetry in the 5-position through preparation of salts.

It has surprisingly been found that by reducing dihydro-1,4-benzodiazepin-2-one derivatives containing a centre of asymmetry in the 3-position new tetrahydro-1,4-benzodiazepin-2-ones can be prepared, which contain centres of asymmetry in the 3- and 5-positions and in which the absolute configuration of the centre in the 5-position is identical with the absolute configuration of the centre in the 3-position which is present also in the starting material.

The process according to the invention is stereospecific, i.e. starting from the 3S, 3R and 3SR dihydrocompounds of the general formula (II), respectively the corresponding 3S,5S; 3R,5R and 3SR,5SR tetrahydrocompounds, respectively can be prepared without resolution.

The compounds of the general formula (II) (wherein $R^1$, $R^2$, $R^3$ and X are as hereinbefore defined) used as starting compounds in the process according to the invention can be prepared by the process disclosed in the Austrian Patent Specification No. 281,035.

The compounds of the general formula (II) can be reduced by reducing agents, which are capable of saturating the 4,5-double bond (azomethine group), without influencing other parts of the molecule. The reduction can for example be carried out with a complex metal hydride, such as sodium borohydride, with a metal and an acid, such as zinc and acetic acids, with nascent hydrogen or by catalytic hydrogenation wherein as a catalyst any conventional metal on the surface of a carrier, such as palladium-on-charcoal catalyst or a metal oxide, such as platinum oxide can be used.

The reduction of the compounds of the general formula (II) is performed in a reaction inert organic solvent, such as an aliphatic alcohol having 1 to 6 carbon atoms, e.g. methanol, ethanol; or an aliphatic carboxylic acid having 1 to 6 carbon atoms, e.g. acetic acid, etc.

The reaction temperature can be varied within a wide range but preferably is between 0° C. and 150° C., more preferably about room temperature. The reaction time strongly depends on the starting compound and solvent employed and on the reaction temperature, and generally is about 1 to 24 hours, preferably 0.5 to 8 hours.

The compounds of the general formula (I), in which $R^4$ represents a hydrogen atom can be converted into acid addition salts by reacting with corresponding acids. The preparation of salts can be used also for the purification of the compounds, and from the acid addition salts obtained, optionally after recrystallisation, the compounds of the general formula (I) can be set free by known methods.

For the preparation of salts for example the following acids can be used: inorganic acids, such as hydrogen halides, e.g. hydrochloric acid, hydrogen bromide; sulfuric acid; phosphoric acid; nitric acid; or perhaloic acids, such as perchloric acid; or organic acids, such as formic acid, acetic acid, propionic acid, glycolic acid, maleic acid, hydroxymaleic acid, fumaric acid, salicilic acid, milk acid, cinnamic acid, benzoic acid, phenylacetic acid, p-amino-benzoic acid, p-hydrobenzoic acid, p-amino-salicilic acid, etc.; alkylsulfonic acids, such as methanesulfonic acid, ethanesulfonic acid, etc.; cycloaliphatic sulfonic acids, such as cyclohexalsulfonic acid; arylsulfonic acids, such as p-toluene-sulfonic acid, naphthylsulfonic acid, sulfanilic acid, etc.; amino acids, such as asparginic acid, glutaminic acid, etc. The acid addition salts can be prepared in any conventional inert organic solvent, which is capable of dissolving the compound of the general formula (I) used as starting compound, and in which the acid addition salt of said compound is insoluble. In this case the acid addition salt precipitated from the reaction mixture can easily be separated by conventional techniques, e.g. filtration. Alternatively, the preparation of acid addition salts can be carried out also in inert organic solvents, in which not only the compounds of the general formula (I) but also their acid addition salts are soluble. In this case the acid addition salt can be precipitated by an apolar organic solvent, e.g. by petroleum ether.

The compounds of the general formula (I) in which $R^4$ stands for a hydrogen atom are preferably reacted with alkali metal cyanates via their acid addition salts. The corresponding compound of the general formula (I) ($R^4$ is hydrogen) is converted into an acid addition salt, preferably hydrogen halide thereof, the salt obtained is separated and suspended or dissolved in an inert organic solvent, such as acetic acid, whereupon the alkali metal cyanate is added to the suspension or solution obtained. As an alkali metal cyanate potassium or sodium cyanate can for example be used.

The reaction temperature can be varied within a wide range but the reaction is preferably performed at about room temperature. The reaction time generally is between 0.5 and 10 hours, depending on the starting compounds, solvent and temperature. The reaction of the compounds of the general formula (I) (wherein $R^1$, $R^2$, $R^3$ and X are as defined above and $R^4$ stands for hydrogen) with phosgene is carried out in an inert organic solvent, such as aromatic hydrocarbons, e.g. benzene, in the presence of an acid binding agent, such as magnesium oxide or sodium hydrogen-carbonate. The compounds of the general formula (I) obtained, in which $R^4$ stands for a chlorocarbonyl group ($R^1$, $R^2$, $R^3$ and X are as defined above) are treated with a concentrated aqueous ammonium hydroxide solution or with a solution of ammonia in an aliphatic alcohol having 1 to 6 carbon atom, preferably methanol, optionally in an inert organic solvent, e.g. an aliphatic alcohol having 1 to 6 carbon atoms. Alternatively, the ammonia solution can also be added to the reaction mixture obtained when preparing the compounds of the general formula (I), in which $R^4$ stands for a chlorocarbonyl group, i.g. the compounds of the general formula (I) need not necessarily be isolated before reaction with ammonia.

The compounds of the general formula (I), in which $R^2$ stands for hydrogen ($R^1$, $R^3$, $R^4$ and X are as hereinabove defined) can be converted into the corresponding 1-alkyl derivatives by reacting with an alkylating agent. As alkylating agents conventional reactants, such as alkyl halides, preferably alkyl iodide, or or dialkyl sulfates can be used. Before carrying out the alkylation the compounds of the general formula (I) are preferably converted into alkali metal derivatives thereof. In this case the compounds are dissolved in an inert organic solvent, such as dioxane, dimethyl formamide, benzene or toluene and are reacted with an alkali metal, alkali metal hydride or alkali metal amide, preferably with sodium or sodium hydride or sodium amide at 0° to 150° C. The alkali metal compound obtained is then reacted with the corresponding alkylating agent.

The new compounds of the general formula (I) can be prepared by the process according to the invention with a good yield, in a well identifiable form. The results of chemical analysis are in good agreement with the calculated values.

The purity of the compounds was controlled by thin layer chromatography. The retention factors ($R_f$) of the compounds illustrated in the working examples were determined on a Stahl GF 254 (Merck) silica gel plate by a 1:1 mixture of ether and dichloromethane. The detection was performed in U.V. light at 254 nm. The melting points were determined in an equipment according to Dr. Tottoli (non-corrected values). For the structural analysis IR, circular dichroism or NMR spectroscopy was used.

The pharmacological properties of the racemic or optically active 1,3,4,5-tetrahydro-2H-1,4-benzodiazepin-2-one derivatives according to the invention, which contain two centres of asymmetry, first of all their excellent enzyme inducing activity, the pregnant reduction of the sedative effect and their low toxicity are illustrated by the following pharmacological tests.

The biological activity and duration of activity of different endogenic and exogenic compounds are greatly influenced by the activity of the NADPH- (nicotinic acid amide-adenine-dinucleotide phosphate-) depending multifunctional oxydase enzyme system of the liver. There are numerous compounds known in the art, showing various pharmacological activities, which are capable of increasing or inducing the activity of the metabolising, multifunctional oxydase enzyme system of the liver [see e.g. Sher, S.P.: Toxicol. appl. Pharmacol. 18, 780 /1971/; G. J. Mannering: in A. Burger's Selected Pharmacological Testing Methods, 51-119 S., Marcel Dekker Inc., New York /1968/]. It is well known that phenobarbital shows an inducing activity in the case of human diseases caused by the defectiveness of the metabolysing enzyme system of the liver. Therefore phenobarbital can successfully be used in the treatment of Czigler-Najjar and Cilbert syndroms and neonatal hyperbilirubinemia, though due to its hypnotic-sedative effect the inducing activity of this compound is not optimal [Vessel and J. E. Page: J. Clin. Invest. 48, 2202 /1969/; J. T. Wilson: Pediatrics 43, 424 /1969/].

For screening the enzyme inducing activity the change in the hexobarbital-induced sleeping time is conventionally measured. The inducing activity of the compounds of the general formula (I) according to the invention was compared to the corresponding activity of phenobarbital and to their own sedative effect, using the following test methods.

Determination of the sleeping time induced by hexobarbital (measurement of enzyme inducing activity)

After (a) one hour and (b) after 24-hour pretreatment with a 40 mg./kg. p.o. dose of the test compounds, the groups of test animals were administered a 60 mg./kg. i.v. dose of hexobarbital. The average sleeping time (±SD) and the percentage change related to the control (%) are given in Table 1 below.

Determination of the potentiation of activity of sodium-barbital (measurement of the sedative activity)

Na-barbital is not metabolised in the liver, thus the potentiation of the activity of Na-barbital can be considered as a direct CNS effect. In the tests carried out [see S. Goldschmidt and R. Wohr: Z. physiol. Chem. 308, 9 /1957/; D. V. Parker: J. Pharm. Pharmac. 27, 729 /1975/] the test animals were pretreated with a 20 mg./kg. i.p. dose of the test compounds of the general formula (I) and after one hour were administered a 100 mg./kg. i.p. dose of Na-barbital. The administered (100 mg./kg.) dose of Na-barbital still has no narcotic effect. The number of the animals falling asleep (in %) is given in Table 2.

Acute toxicity (p.o.)

To the test animals 250 and 500 mg./kg. doses, resp. of the test compounds were administered orally and the number of the dead animals was registered for 14 days. The results are shown in Table 3.

As test animals CFLP male mice weighing 8 to 22 g. were used.

TABLE 1

| Test Compound (Example No.) | Dose mg./kg. p.o. | Hexobarbital-sleeping time (min.) | | | |
|---|---|---|---|---|---|
| | | 1-hour pre-treatment | | 24-hour pre-treatment | |
| | | average ± SE | Δ% | average ± SE | Δ% |
| Control | 0 | 35 ± 2.38 | | 34 ± 2.60 | |
| 1 | 40 | 67.2 ± 7.01 | +91$^x$ | 19.5 ± 1.84 | −43 |
| 2 | 40 | 61.2 ± 5.21 | +73$^x$ | 13.3 ± 0.54$^x$ | −61 |
| 3 | 40 | 43.3 ± 4.18 | +23 | 12.0 ± 0.83$^x$ | −65 |
| 4 | 40 | 43.3 ± 5.01 | +23 | 9.9 ± 0.62$^x$ | −71 |
| 5 | 40 | 37.3 ± 3.01 | +6 | 9 ± 0.43$^x$ | −73 |
| Phenobarbital | 40 | 86.2 ± 7.51 | +145 | 11.2 ± 0.35$^x$ | −69 |

($^x$ p < 0.001 compared to the control)

TABLE 2

| Text compound (Example No.) | Dose mg./kg. i.p. | Number of the test animals fallen asleep in % of the control |
|---|---|---|
| 1 | 20 | 50 |
| 2 | 20 | φ |
| 3 | 20 | 0 |
| 4 | 20 | φ |
| 5 | 20 | 20 |
| Phenobarbital | 20 | 60 |

TABLE 3

| Test compound (Example No.) | LD$_{50}$ mg./kg. p.o. |
|---|---|
| 1 | <500 |
| 2 | <500 |
| 3 | <500 |
| 4 | <500 |
| 5 | <500 |
| Phenobarbital | 190.9 |

The known compounds having enzyme inducing activity generally show an inhibiting effect immediately after administration, which results in the prolongation of the sleeping time.

From the data listed in Table 1 it can clearly be seen that in the case of the compounds according to the invention the sleeping time determined after 1 hour after administration is only slightly increased. In this respect the compounds of Examples 3, 4 and 5 have the most favourable properties. It can also be seen that phenobarbital increases the sleeping time to almost 3-times of its original value. 24 hours after administration the compounds according to the invention show the same enzyme inducing activity as phenobarbital, therefore the decomposition of hexobarbital in the organism is accelerated and accordingly the sleeping time is reduced.

The sleeping time induced by hexobarbital, in addition to the decomposition time of hexobarbital in the liver can also be influenced by a CNS activity. From Table 2 it can be concluded that the test compounds when compared to phenobarbital, have a very small, almost negligible sedative effect. Accordingly, the main biological effect of the compounds is their enzyme inducing activity.

The data of Table 3 unambiguously prove that the compounds according to the invention are far less toxic than phenobarbital.

To sum it up, it can be concluded that after a 24 hours pretreatment the new compounds of the general formula (I) according to the invention show approximately the same enzyme inducing activity as phenobarbital. Their main advantage is, however, that after a 1-hour pretreatment they potentiate less or (see the compounds of Examples 3 to 5) not al all the activity of hexobarbital, in other words they are practically devoid of the disadvantageous inhibiting period, which is generally characteristic of the known compounds having enzyme inducing activity. A further advantage of the instant compounds that they show no sedative activity and are far less toxic than phenobarbital.

The compounds of the general formula (I) can be used in the therapy in the form of pharmaceutical compositions containing these active ingredients in admixture with solid or liquid carriers and/or other additives. The compositions are prepared by methods of pharmaceutical industry known per se.

The pharmaceutical compositions can be formulated in forms suitable for parenteral or enteral administration. As carriers for example water, gelatine, lactose, milk sugar, starch, pectine, magnesium stearate, stearic acid, talc, vegetable oils, such as peanut oil, olive oil, etc. can be used. The compositions may be finished in the form of solid, e.g. tablets, lozenges, dragees, capsules, such as hard gelatine capsule, suppositories, etc. or liquid, e.g. oily or aqueous solutions, suspensions, emulsions, syrups, soft gelatine capsules, injectable oily or aqueous solutions or suspensions, etc. formulations. The quantity of the solid carrier can be varied within a wide range but preferably is about between 25 mg. and 1 g. The pharmaceutical compositions optionally can contain also conventional pharmaceutical additives, such as preservatives, stabilizing, wetting, emulsifying agents, salts capable of adjusting the osmotic pressure, buffers, flavouring agents, aroma agents, etc. Optionally further pharmaceutically active compounds can also be present in the formulations.

The pharmaceutical compositions are preferably finished as unit doses, which correspond to the desired route of administration. The pharmaceutical compositions are prepared by conventional techniques, which comprise for example screening, admixing, granulating, pressing or dissolving of the components. The compositions obtained can be subjected to further operations conventionally used in the pharmaceutical industry, for example sterilization.

Further details of the present invention are to be found in the following Examples. It is, however, by no means intended to limit our invention to the Examples.

EXAMPLE 1

3S,5S-1,3-Dimethyl-5-phenyl-7-chloro-1,3,4,5-tetrahydro-2H-1,4-benzodiazepin-2-one 10 g. of 3S-1,3-dimethyl-5-phenyl-7-chloro-1,3-dihydro-2H-1,4-benzodiazepin-2-one are dissolved in 50 ml. of acetic acid and to the solution obtained 5 g. of sodium borohydride is portionwise added, with stirring, under cooling. Stirring is continued for a further half an hour, whereupon the mixture is neutralized with a 8% aqueous sodium hydrogencarbonate solution under ice cooling. The slowly solidifying product is filtered off, washed with water and is subsequently dried. 9.5 g. of the title compound are obtained, melting at 102° to 103° C. (after recrystallization from ethanol).

Yield: 95.65%. $[\alpha]_D^{25} = +318.9$ (c=1.03, chloroform)

Analysis for $C_{17}H_{17}N_2OCl$ (molecular weight: 300.79): calculated: C=67.88%, H=5.69%, N=9.31%. found: C=67.72%, H=7.05%, N=9.49%.

EXAMPLE 2

3R,5R-1,3-Dimethyl-5-phenyl-7-chloro-1,3,4,5-tetrahydro-2H-1,4-benzodiazepin-2-one 5 g. of 3R-1,3-dimethyl-5-phenyl-7-chloro-1,3-dihydro-2H-1,4-benzodiazepin-2-one are dissolved in 50 ml. of acetic acid and to the stirred solution 5 g. of zinc powder are added, under cooling with water. Stirring is continued for further one hour, whereupon the mixture of zinc and zinc salt is filtered off in the filtrate acetic acid is neutralized by a 8% aqueous sodium hydrogencarbonate solution under ice cooling. The slowly solidifying product is filtered off, washed with water and dried.

4.28 g. of the title compound are obtained, melting at 102° to 104° C. (after recrystallization from ethanol).

Yield: 86.29%, $[\alpha]_D^{25} = -322.6$ (c=1.015, chloroform), $R_f = 0.58$.

Analysis for $C_{17}H_{17}N_2OCl$ (molecular weight: 300.79): calculated: C=67.88%, H=5.69%, N=9.31%. found: C=67.75%, H=6.95%, N=9.35%.

EXAMPLE 3

3S,5S-1,3-Dimethyl-4-carbamoyl-5-phenyl-7-chloro-1,3,4,5-tetrahydro-2H-1,4-benzodiazepin-2-one 1.5 g. (4.97 mmoles) of 3S,5S-1,3-dimethyl-5-phenyl-7-chloro-1,3,4,5-tetrahydro-2H-1,4-benzodiazepin-2-ones are dissolved in a mixture of 10 ml. of ethanol and 2 ml. of ether and to the solution dry hydrochloric acid gas is introduced. After cooling with ice for 10 minutes the precipitated hydrochloride is filtered off and suspended in 10 ml. of acetic acid without previous drying. To the suspension 0.5 g. (6.16 mmoles) of potassium cyanate are portionwise added, under cooling with water and the mixture is stirred for 4 hours. Thereafter 50 g. of ice pieces are added to the mixture and it is neutralized with a concentrated aqueous ammonium hydroxide solution. The product, which solidifies upon cooling is filtered off, washed with water and dried. 1.4 g. of the title compound are obtained, melting at 208° to 209° C. (after recrystallization from ethanol).

Yield: 81.87%, $[\alpha]_D^{25} = -552.9$ (c=0.897, chloroform), $R_f = 0.06$.

Analysis for $C_{18}H_{18}N_3O_2Cl$ (molecular weight: 343.82): calculated: C=62.88%, H=5.28%, N=12.22%. found: C=62.65%, H=6.68%, N=12.07%.

EXAMPLE 4

3R,5R-1,3-Dimethyl-4-carbamoyl-5-phenyl-7-chloro-1,3,4,5-tetrahydro-2H-1,4-benzodiazepin-2-one Following the procedure described in Example 3 but starting from 1.5 g. of 3R,5R-1,3-dimethyl-5-phenyl-7-chloro-1,3,4,5-tetrahydro-2H-1,4-benzodiazepin-2-one, the title compound is obtained, melting at 207° to 208° C. $[\alpha]_D^{25} = +550.4$ (c=1.19, chloroform), $R_f = 0.06$.

EXAMPLE 5

3RS,5RS-1,3-Dimethyl-4-carbamoyl-5-phenyl-7-chloro-1,3,4,5-tetrahydro-2H-1,4-benzodiazepin-2-one Following the procedure described in Example 3 but starting from 1.5 g. of 3RS,5RS-1,3-dimethyl-5-phenyl-7-chloro-1,3,4,5-tetrahydro-2H-1,4-benzodiazepin-2-one, the title compound is obtained, melting at 241° to 242° C. $R_f = 0.06$.

We claim:

1. An optically active or racemic compound of the formula (I)

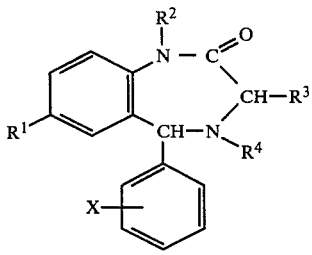

wherein
R[1] stands for hydrogen, halogen, trifluoro-methyl or a nitro group;
R[2] stands for hydrogen or alkyl having 1 to 6 carbon atoms;
R[3] is methyl, isopropyl, isobutyl, sec-butyl, benzyl, hydroxymethyl, β-hydroxyethyl, p-hydroxybenzyl, carbamoylmethyl, β-carbamoylethyl, carboxymethyl, β-carboxylethyl, mercaptomethyl, β-methylthioethyl, 4-amino-n-butyl, 3-guanidino-n-propyl, 3-indolylmethyl and 4-imidazolylmethyl;
R[4] is hydrogen, chlorocarbonyl or carbamoyl; and
X is hydrogen, halogen or trifluoro-methyl, with the proviso that if in the racemic compounds R[4] stands for hydrogen R[3] is other than alkyl having 1 to 6 carbon atoms, in which the centres of asymmetry in the 3- and 5-positions have the same absolute configuration, and pharmaceutically acceptable acid addition salts thereof.

2. 3RS,5RS-1,3-Dimethyl-4-carbamoyl-5-phenyl-7-chloro-1,3,4,5-tetrahydro-2H-1,4-benzodiazepin-2-one and pharmaceutically acceptable acid addition salts thereof.

3. 3R,5R-1,3-Dimethyl-4-carbamoyl-5-phenyl-7-chloro-1,3,4,5-tetrahydro-2H-1,4-benzodiazepin-2-one and pharmaceutically acceptable acid addition salts thereof.

4. 3S,5S-1,3-Dimethyl-4-carbamoyl-5-phenyl-7-chloro-1,3,4,5-tetrahydro-2H-1,4-benzodiazepin-2-one and pharmaceutically acceptable acid addition salts thereof.

5. 3R,5R-1,3-Dimethyl-5-phenyl-7-chloro-1,3,4,5-tetrahydro-2H-1,4-benzodiazepin-2-one and pharmaceutically acceptable acid addition salts thereof.

6. 3S,5S-1,3-Dimethyl-5-phenyl-7-chloro-1,3,4,5-tetrahydro-2H-1,4-benzodiazepin-2-one and pharmaceutically acceptable acid addition salts thereof.

7. Pharmaceutical composition having enzyme inducing activity, which comprises as an active ingredient an effective amount of at least one racemic or optically active compound of the general formula (I) (wherein R[1], R[2], R[3], R[4] and X have the same meaning as defined in claim 1), or a pharmaceutically acceptable acid addition salt thereof, in admixture with inert solid or liquid pharmaceutical carrier.

8. Pharmaceutical composition according to claim 7 characterized by containing as active ingredient 3RS,5RS-1,3-dimethyl-4-carbamoyl-5-phenyl-7-chloro-1,3,4,5-tetrahydro-2H-1,4-benzodiazepin-2-one.

9. Pharmaceutical composition according to claim 7 characterized by containing as active ingredient 3R,5R-1,3-dimethyl-4-carbamoyl-5-phenyl-7-chloro-1,3,4,5-tetrahydro-2H-1,4-benzodiazepin-2-one.

10. Pharmaceutical composition according to claim 7 characterized by containing as active ingredient 3S,5S-1,3-dimethyl-4-carbamoyl-5-phenyl-5-chloro-1,3,4,5-tetrahydro-2H-1,4-benzodiazepin-2-one.

* * * * *